(12) United States Patent
Labrie et al.

(10) Patent No.: US 10,016,136 B2
(45) Date of Patent: Jul. 10, 2018

(54) IMAGE RELAYING CANNULA WITH DETACHABLE SELF-ALIGNING CONNECTOR

(71) Applicant: Optomak, Inc., Quebec (CA)

(72) Inventors: Jonatan Labrie, St-Henri (CA); Harold Dehez, Quebec (CA); Sead Doric, Ancienne-Lorette (CA)

(73) Assignee: OPTOMAK, INC. (CA)

( * ) Notice: Subject to any disclaimer, the term of this patent is extended or adjusted under 35 U.S.C. 154(b) by 1025 days.

(21) Appl. No.: 14/310,012

(22) Filed: Jun. 20, 2014

(65) Prior Publication Data
US 2015/0366437 A1 Dec. 24, 2015

(51) Int. Cl.
| | |
|---|---|
| A61B 5/055 | (2006.01) |
| A61B 5/00 | (2006.01) |
| A61B 1/00 | (2006.01) |
| A61B 5/053 | (2006.01) |
| A61B 1/06 | (2006.01) |

(52) U.S. Cl.
CPC ........ *A61B 5/0084* (2013.01); *A61B 1/00167* (2013.01); *A61B 1/0615* (2013.01); *A61B 5/0071* (2013.01); *A61B 5/0538* (2013.01); *A61B 5/688* (2013.01); *A61B 5/6865* (2013.01); *A61B 2560/0443* (2013.01); *A61B 2562/228* (2013.01)

(58) Field of Classification Search
CPC .. A61B 5/0066; A61B 5/0084; A61B 5/00165
See application file for complete search history.

(56) References Cited

U.S. PATENT DOCUMENTS

| | | | |
|---|---|---|---|
| 4,878,485 A | 11/1989 | Adair | |
| 5,145,227 A | 9/1992 | Monford, Jr. | |
| 5,213,092 A | 5/1993 | Uram | |
| 5,411,500 A | 5/1995 | Lafferty et al. | |
| (Continued) | | | |

FOREIGN PATENT DOCUMENTS

| | | |
|---|---|---|
| WO | WO 2013082156 A1 | 6/2013 |
| WO | WO 2014071390 A1 | 5/2014 |

OTHER PUBLICATIONS

Muldoon, et al., "Subcellular-resolution molecular imaging within living tissue by fiber microendoscopy", Optics Express, Dec. 10, 2007, 11 pages (pp. 1-11 in pdf), vol. 15, No. 25, Optical Society of America, US.

(Continued)

*Primary Examiner* — Michael D Abreu
(74) *Attorney, Agent, or Firm* — Mitch Harris, Atty at Law, LLC; Andrew M. Harris

(57) ABSTRACT

An optical cannula configured for implantation in biological tissue or other samples provides minimal invasiveness while accessing image deep structures within the sample. The cannula has a stabilizer portion that is used to affix the cannula to the sample, and an extension portion that protrudes into the sample and is either formed by, or contains, an optical probe that images a target area within the sample to an object image provided to an external optical device. The cannula has an integrated coupler portion that detachably connects to a connector of the external device, providing removable and interchangeable connection to external optical systems.

21 Claims, 8 Drawing Sheets

(56) References Cited

U.S. PATENT DOCUMENTS

| | | | |
|---|---|---|---|
| 5,457,576 | A | 10/1995 | Atkinson et al. |
| 5,704,892 | A | 1/1998 | Adair |
| 5,868,742 | A * | 2/1999 | Manes .................. A61B 18/16 606/41 |
| 6,370,422 | B1 | 4/2002 | Richards-Kortum et al. |
| 6,503,196 | B1 | 1/2003 | Kehr et al. |
| 6,643,071 | B2 | 11/2003 | Schnitzer |
| 6,863,651 | B2 | 3/2005 | Remijan et al. |
| 6,929,604 | B2 | 8/2005 | Stone et al. |
| 7,091,500 | B2 | 8/2006 | Schnitzer |
| 7,307,774 | B1 | 12/2007 | Schnitzer et al. |
| 7,336,988 | B2 | 2/2008 | Schnitzer |
| 7,353,067 | B1 * | 4/2008 | Helland ............... A61N 1/0558 607/130 |
| 7,447,539 | B2 | 11/2008 | Genet et al. |
| 7,511,891 | B2 | 3/2009 | Messerschmidt |
| 7,969,659 | B2 | 6/2011 | Jacobsen et al. |
| 8,346,346 | B1 | 1/2013 | Schnitzer et al. |
| 2004/0143190 | A1 | 7/2004 | Schnitzer |
| 2006/0119734 | A1 | 6/2006 | Neel |
| 2010/0121153 | A1 * | 5/2010 | To ......................... A61B 10/06 600/214 |
| 2012/0062723 | A1 | 3/2012 | Ghosh et al. |
| 2012/0065495 | A1 | 3/2012 | Richards-Kortum et al. |

OTHER PUBLICATIONS

Flusberg, et al., "High-speed, miniaturized fluorescence microscopy in freely moving mice", Nature Methods, Oct. 2008, pp. 1-4, Nature Publishing Group, London.

Murayama, et al., "In vivo dendritic calcium imaging with a fiberoptic periscope system", Nature Protocols., Oct. 2009, pp. 1551-1559, vol. 4, No. 10, Nature Publishing Group, London.

Barretto, et al., "Time-lapse imaging of disease progression in deep brain areas using fluorescence microendoscopy", Nature Medicine, Feb. 2011, pp. 223-228, vol. 17, No. 2, Nature Publishing Group, London.

Ghosh, et al., "Miniaturized integration of a fluorescence microscope", Nature Methods, Oct. 2011, pp. 871-882, vol. 8, No. 10, Nature Publishing Group, London.

Jung, et al., "Multiphoton endoscopy", Optics Letters, Jun. 2003, pp. 902-904, vol. 28, No. 11, Optical Society of America, US.

Ziv, et al., "Long-term dynamics of CA1 hippocampal place codes", Nature Neuroscience, Feb. 2013, 5 pages (pp. 1-5 in pdf), 16(3).

Muguruma, et al., "Endoscopic Molecular Imaging: Status and Future Perspective", Clinical Endoscopy, Nov. 2013, pp. 603-610, vol. 46, No. 6, Korean Society of Gastrointestinal Endoscopy, Seoul, Korea.

"nVistaHD: See the Brain in a New Light", downloaded from: http://www.inscopix.com/sites/default/files/downloads-nvistainvista_hd_booklet_nb-201402.1_0.pdf on Apr. 22, 2014, 16 pages. (pp. 1-16 in pdf).

* cited by examiner

IMAGE RELAYING CANNULA WITH DETACHABLE SELF-ALIGNING CONNECTOR

BACKGROUND OF THE INVENTION

1. Field of the Invention

The present invention is related generally to biological microscopy, and in particular to a cannula for detachably connecting and aligning an optical device to a biological sample.

2. Background of the Invention

When making microscopic observations of in vivo biological specimens, minimally invasive techniques are required. However, conventional microscopes feature large size microscope objectives. Large objectives cannot be implanted within a sample without causing significant damage to the sample, such as removing structures in order to facilitate access to deep layers within the sample. Less invasive fiber-optic cannulae that are typically used in optogenetics experiments are typically configured only for optical stimulation or silencing of a certain class of neurons.

Existing optical devices that relay an image outside of a sample are either implanted directly in the sample or inserted in a metallic tube terminating with an optical window. Alternatively, or in combination with the above, specific external components such as miniaturized microscopes have been mounted directly to a sample.

SUMMARY OF THE INVENTION

The invention includes an optical cannula for attachment to a biological sample, devices including the optical cannula and a method of using the optical cannula.

The optical cannula includes a stabilizer portion adapted for mounting the optical cannula to the sample and an extension portion that extends from a plane of the stabilizer portion. The stabilizer portion is securable to the sample at the extension a distance above the surface of the sample and outside of the sample. The optical cannula also includes an optical probe extending through the stabilizer with a distal end extending into the biological sample. The other proximal end of the probe terminates near or in the extension portion. The optical cannula includes a coupling for detachably securing an external optical device to the extension portion, wherein the external optical device is optically coupled to the proximal end of the optical probe and aligned with an optical axis of the optical probe by the attachment to the coupling.

The foregoing and other objectives, features, and advantages of the invention will be apparent from the following, more particular, description of the preferred embodiment of the invention, as illustrated in the accompanying drawings.

BRIEF DESCRIPTION OF THE DRAWINGS

The novel features believed characteristic of the invention are set forth in the appended claims. The invention itself, however, as well as a preferred mode of use, further objectives, and advantages thereof, will best be understood by reference to the following detailed description of an illustrative embodiment when read in conjunction with the accompanying drawings, wherein like reference numerals indicate like components, and:

DESCRIPTION OF ILLUSTRATED EMBODIMENT

The present invention concerns an optical cannula for coupling an image taken within a biological sample, generally an in vivo biological sample, to an optical system or device, such as a microscope. In order to provide minimal invasiveness with respect to the sample, but in order to reach deep tissues, the cannula includes an extension portion that projects into the sample and a stabilizer portion at which the cannula is mounted to the sample. The cannula features an optical probe that extends through the extension portion and serves as a relay imaging system that relays an image of structures located at the distal end of the extension portion of the cannula to the proximal end of the probe. The optical cannula can be used for image magnification and recording and may also be coupled to an illumination source to optically excite specific areas within a sample. Alternatively, or in combination the cannula may provide coupling for electrodes for electrical stimulation or measurement and recording of electrical properties within the sample or liquid tubing to provide for application or removal of fluids. In order to provide flexibility with respect to the above applications, optical cannula includes a detachable coupling that provides for simple connection to and disconnection from external components.

Figure 1:
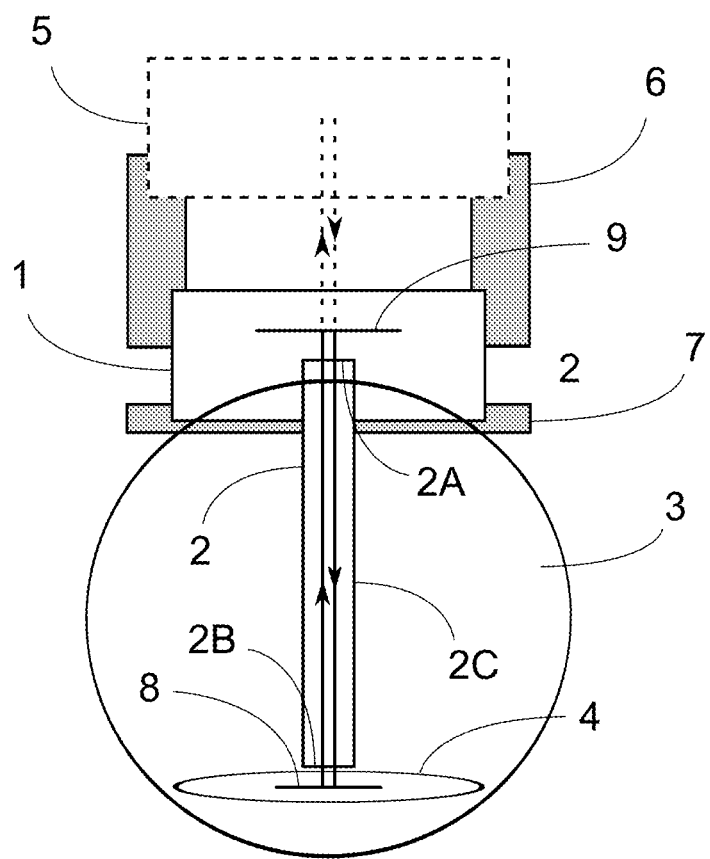
FIG. 1 is a side cross-section drawing depicting an exemplary optical cannula.

Referring now to FIG. 1, an exemplary optical cannula 1, is shown. Optical cannula 1 provides a housing that includes a stabilizer portion 7, which is used to affix optical cannula 1 to a sample 3, generally by applying an adhesive between the face of stabilizer portion 7 and the outer surface of sample 3 facing stabilizer portion 7. The housing provided by optical cannula 1 also includes an extension portion 2 that extends within sample 3 and an optical probe 2C that extends through extension portion 2 in a direction perpendicular to the plane of stabilizer portion 7, which in the depicted embodiment is a relay lens that forms extension portion 2, and which may be a gradient-index (GRIN) lens, rigid fiber bundle or other suitable imaging probe. Optical cannula 1 provides easy and interchangeable access an image of an optical object plane 8 within a target area 4 of sample 3. A distal end 2B of the optical probe 2C forming extension portion 2 images sample 3 at optical object plane 8 and conducts the image to an object image plane 9 outside of sample 3. A proximal end 2A of the optical probe 2C forming extension portion 2 images a spot on optical object plane 8 of target area 4 that can be coupled to an external device 5 such as a microscope, illumination source, another imaging conduit, etc. A detachable connection 6 is provided by the housing of optical cannula 1 for connection of an external device 5 to optical cannula 1 for interchangeability and ease of installation, since optical cannula 1 can be installed without external device 5 attached, as will be described in further detail below. The configuration of detachable connection 6 is such that an optical image plane 9 will self-align with an imaging plane of external device 5, when the detachable connection couples external device 5 to optical cannula 1. Sufficient clearance is provided for optics that may be included within external device 5, in particular, clearance is provided for the maximum volume the optics of the external device 5 can be allowed to extend into cannula 1. For applications involving external optics localized close to proximal end 2A of optical probe 2C, the imaging cannula is configured to provide enough clearance above proximal end 2A. The ends, 2A, 2B of optical probe 2C are generally covered with an anti-reflective coating, and the cylindrical outside surface of optical probe is generally covered with an optically absorptive coating or is sheathed in a tube, which may be e.g., stainless steel tube, or polyimide tube.

Figure 2:
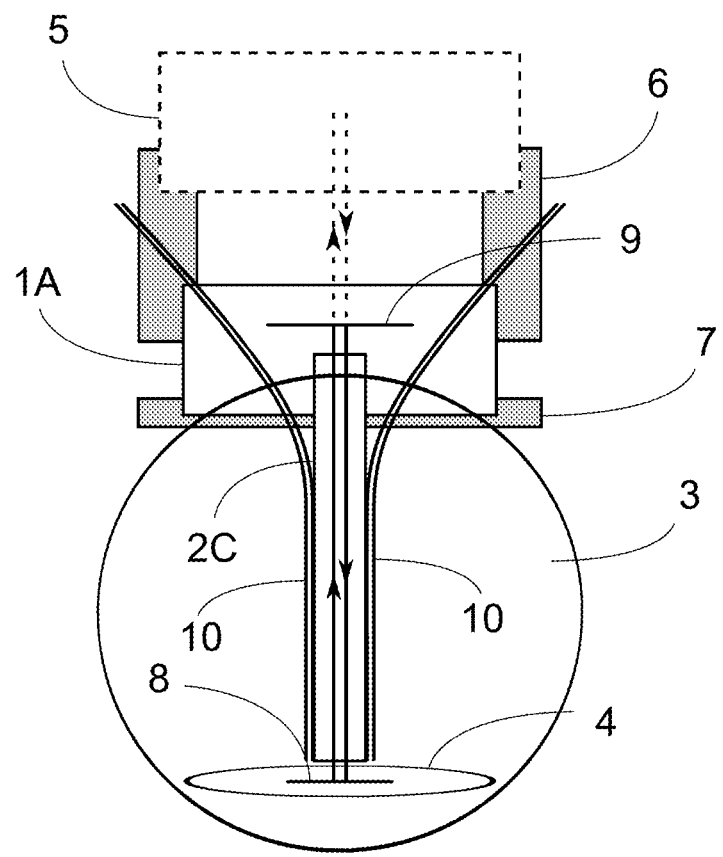
FIG. 2 is a side cross-section drawing depicting another exemplary optical cannula.

Referring now to FIG. 2, another example of an optical cannula 1A, is shown. Optical cannula 1A of FIG. 2 is similar to optical cannula 1 of FIG. 1, so only differences between the exemplary cannulae are shown. In optical cannula 1A, extension portion 2 further includes fluid tubing and/or electrodes 10 that can be used to introduce or remove fluids and/or to provide electrical stimulation or measurement/recording within sample 3. In one embodiment of the invention, tubing and/or electrodes 10 is provided as capillaries and are fixed on the optical probe 2. Smaller diameter fluid tubing is then inserted inside of the capillaries. A hybrid electrical-imaging cannula can also be obtained with the insertion of an electrode using the same tubing.

Figure 3A:
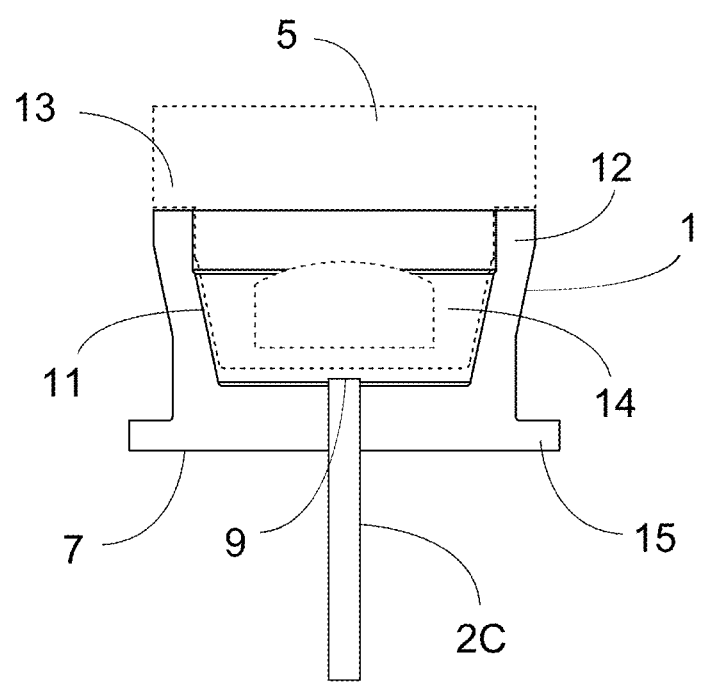
FIG. 3a is side cross-section drawing depicting details of an optical cannula.

Referring now to FIG. 3, a side cross-section view of exemplary optical cannula 1 is shown. Details shown in FIG. 3 are also applicable to exemplary embodiments of optical cannula 1A of FIG. 2. A tapered portion 11 of the internal surface of optical cannula 1 is tapered so that when external device 5 is being attached to optical cannula 1, optics 14 of external device 5 will automatically align with proximal end 2A of optical probe 2C. A cylindrical portion 12 of the internal surface of optical cannula 1 is provided to complete the alignment of optics 14 of external device 5 with object image plane 9 provided by the proximal end 2A of optical probe 2C. External device 5 is inserted until contact is made between a shoulder portion 13 of external device 5 and cylindrical portion 12 of optical cannula 1. A flange 15 provides an increase in the area of the stabilizing portion of cannula 1A, at which point cannula 1A may be glued to sample 3 and flange 15 increases the attachment provided by the adhesive.

Figure 3B:
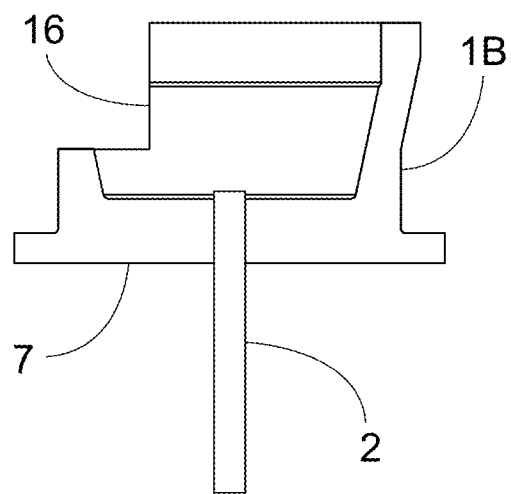
FIG. 3b is side cross-section drawing depicting further details of an optical cannula.

Referring now to FIG. 3B, another exemplary embodiment of an optical cannula 1B is shown, in which an orientation key 16 may be formed at a portion of the circumference of optical cannula 1 of FIG. 1 or optical cannula 1A of FIG. 2. Orientation key 16 aligns with a matching projection on external device 5 (not shown). Orientation key 16 thus provides rotational alignment between optical object plane 8 and optical image plane 9 as shown in FIG. 1, and also may provide for alignment of fluid tubing and/or electrodes 10 as provided in optical cannula 1A as shown in FIG. 2.

Figure 4:
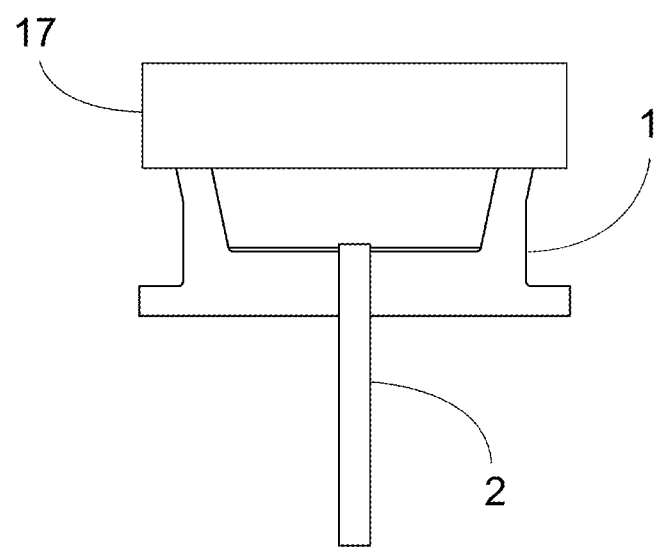
FIG. 4 is a side cross-section drawing depicting an optical cannula with a protective cap installed.

FIG. 4 shows optical cannula 1 with a protective cap 17 installed that provides protection of the optics of optical cannula 1, particularly proximal end 2A of optical probe 2C while measurements are not being made with an external device 5. Protective cap 17 makes it possible to install optical cannula 1 in one procedure and location, with subsequent attachment to an external device 5 such as a microscope. Protective cap 17 also makes it possible to cover optical cannula 1 while changing external device 5 and to share a single external device 5 such as a relatively costly microscope among multiple samples.

Figure 5:
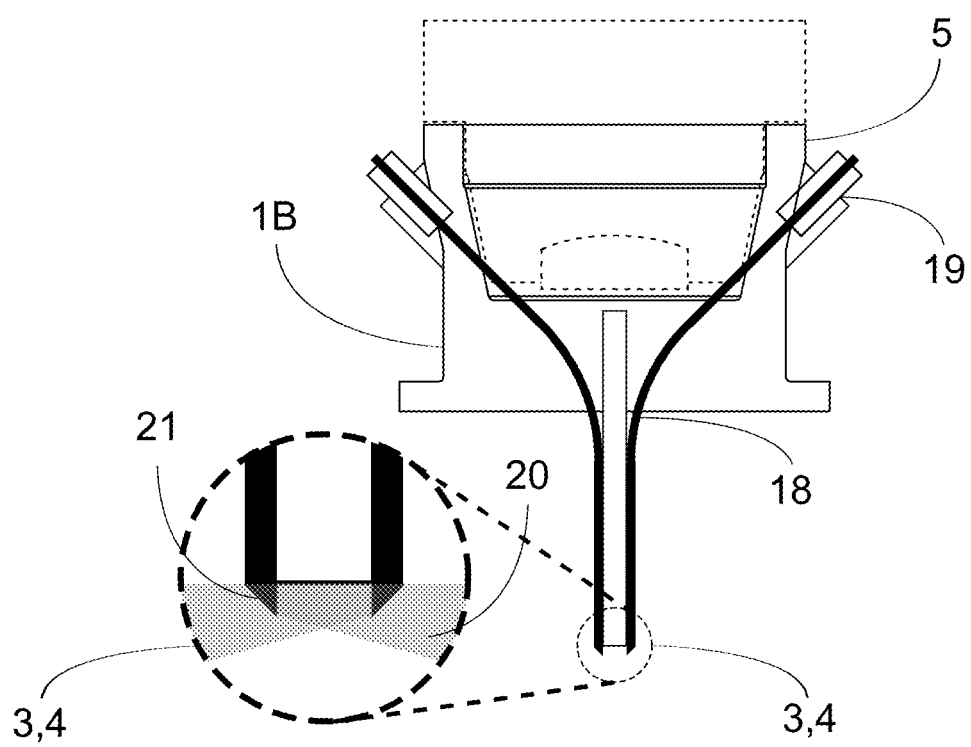
FIG. 5 is a side cross-section drawing depicting yet another exemplary optical cannula.

FIG. 5 shows another exemplary optical cannula 1B with integrated side-illuminating optical fibers 18 and detachable fiber optic connectors 19 to provide illumination of target area 4 of sample 3 by illuminating light beams 20 provided from cleaved and polished distal ends 21 of optical fibers 18. The cleavage angle may be 45 degrees, for example, providing illumination light beams 20 that are perpendicular to the imaging axis of optical probe 2. By providing a detachable attachment for both external device 5 and optical fibers 18, optical cannula 1B provides interchangeable operation when installed on sample 3. To compensate for the absorption and the diffusion of light within the sample, at least two illumination fibers are disposed on opposite sides of optical probe 2. Area of illumination is increased by adding new illumination fibers or by increasing the core diameter of the fibers. In one embodiment, fiber optic sleeves or miniaturized M3 fiber-optic connectors 19 are used to connect the illumination optical fibers 18 to external fiber optic patch cords.

In another exemplary embodiment that can also be provided in combination with optical fibers 18, liquid tubes or electrodes can replace detachable fiber optic connectors 19 and fluid or electrical conductors (e.g., barbed tubing connectors or wires) can replace optical fibers 18 to provide a detachable liquid injector or electrical probe within cannula 1B that can be used to stimulate sample 3. In the fluid-injection embodiment described above, in vivo in situ immune-fluorescence imaging can be performed. A solution containing labeled monoclonal antibodies specific for molecular markers of interest is perfused at the tip of optical cannula 1B. Washing solution is then injected to remove the excess antibodies that are not linked to target antigen. The immune-labeled target area can then be observed by fluorescence imaging. The same embodiment can also be used to perform fluorescence imaging with labeled peptide, activation probe or nano-particles, or stimulated neuron with Designer Receptors Exclusively Activated by Designer Drugs (DREADD) with an improved spatial and temporal resolution compared to regular systemic injection of the designer drugs. Calcium imaging as well as electrophysiological and optogenetic stimulation and recording may also be performed with embodiments of the invention that include both electrode and fluid tubing.

Figure 6:
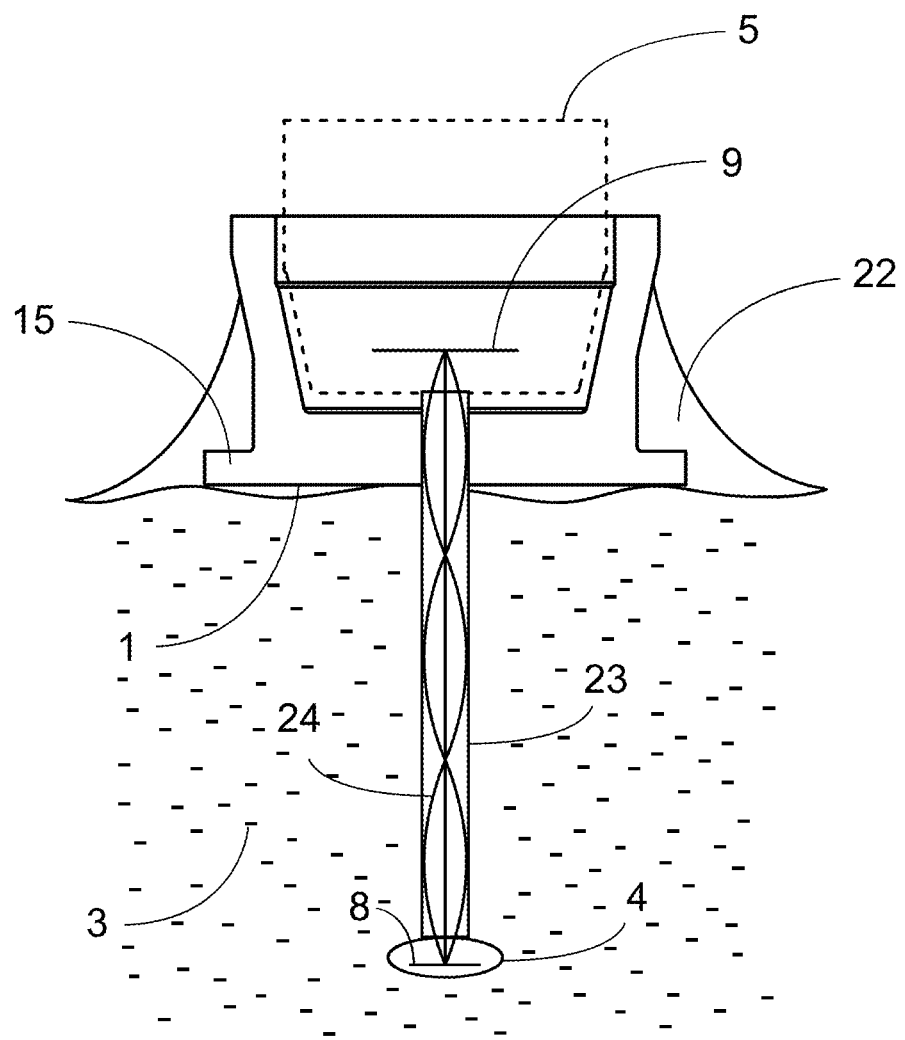
FIG. 6 is a side cross-section drawing depicting an optical cannula installed on a sample.

FIG. 6 shows another view of exemplary cannula 1 of FIG. 1, showing details which may also be applied to optical cannula 1A of FIG. 2 and optical cannula 1B of FIG. 5. FIG. 6 shows an adhesive 22 used to affix cannula 1 to sample 3. In the particular example shown in FIG. 6, optical probe 2C is provided by a GRIN lens 23. Rays 24 propagate within GRIN lens 23 to provide the optical coupling between target object plane 8 and optical image plane 9 and thus couple an image of target object plane 8 to external device 5.

Figure 7:
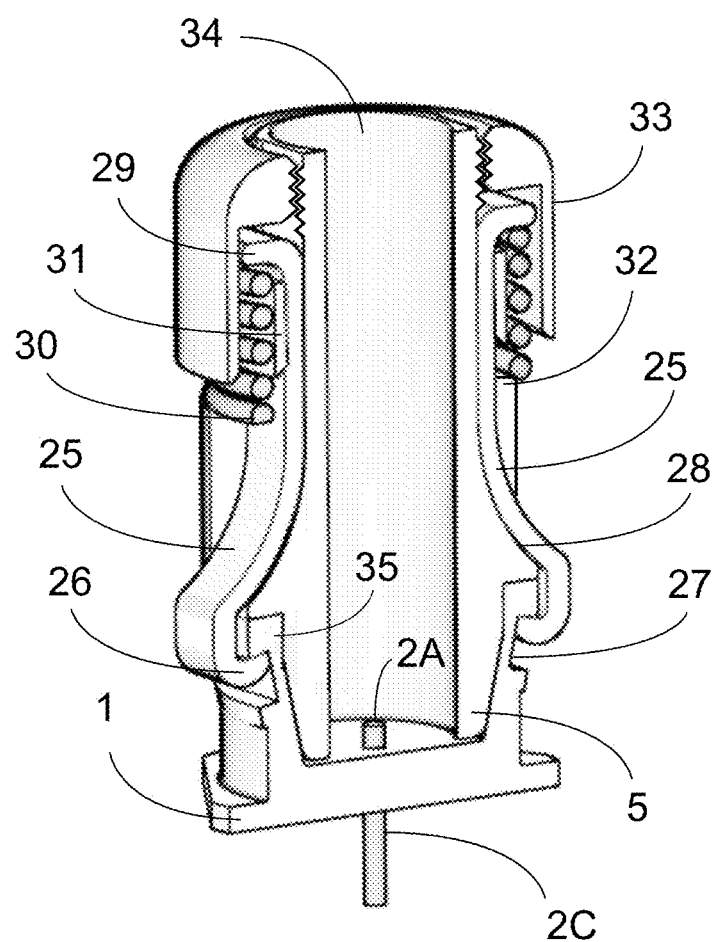
FIG. 7 is a side perspective sectional view of an exemplary optical cannula.

FIG. 7 shows further details of exemplary cannula 1 of FIG. 1, showing details which may also be applied to optical cannula 1A of FIG. 2 and optical cannula 1B of FIG. 5. FIG. 7 shows a particular detachable connector arrangement that is provided on external device 5. Detachability is provided by latches 25 that secure external device 5 to cannula 1. Latches 25 comprise extensions extending along an outside surface of the detachable connector. Latches 25 terminate in hooks 26 that capture a shoulder 35 formed around the cylindrical portion of cannula 1. In the illustration, an inner void 34 provides for integration of the optics of external device 5, which is generally a lens that couples to proximal end 2A of optical probe 2C and may be an end of another optical fiber bundle or GRIN lens. Alternatively, the proximal end of optical probe 2C may project an image directly onto an image sensor or lens system integrated within inner void 34. A slot 27 below the shoulder 35 secures hooks 26 of latches 25, which may be made of spring steel and pre-stressed to provide a retaining force against the inner surface of slot 27. When a locking nut 33 is spun onto cannula 1 toward sample 3, latches 25 slide along a conical outer surface 28 of cannula 1, causing hooks 26 to disengage from slot 27. Conical outer surface 28 is arranged with the proper acute angle to cause expansion of latches 25 as the ends of latches 25 opposing hooks 26 are compressed toward sample 3 by a locking nut 33. When locking nut 33 is loosened, hooks 26 are relaxed back into slot 27 unless external device 5 has been removed from cannula 1. A compression spring 30 provides additional restoring force to cause latches 25 to be pulled back toward locking nut 33. Compression spring 30 is secured by a spring retaining ring 31 and rests on a shoulder 32 of the body of external device 5. Compression spring 30 applies force against a shoulder 29 formed on the ends of latches 25 opposite hooks 26. Locking nut 33 also prevents latches 25 from sliding off of the connector assembly of external device 5 once the cannula 1 is released from external device 5. As an alternative to the locking nut arrangement (or in the depicted embodiment, as well) pliers can be used to compress latches to expand hooks 26 to release cannula 1 from external device 5.

The detachable implementation of the cannula illustrated in FIG. 7, along with the stabilizer/optical probe integration illustrated in the other figures, provides an image relay configured for precise connection with a plurality of external components. Unlike existing micro-endoscopes, cannula 1 is configured to easily connect to or disconnect from external device 5 with precise and repeatable alignment and does not require protective tubing nor a protective window, thereby reducing the invasiveness of related surgical procedures. In the exemplary embodiment, the outer diameter of the implantable part of the imaging cannula is less than 600 microns and the length of optical probe 2 is less than 10 mm. The weight of the cannula is generally under 0.5 g and the volume less than 0.1 cm³

As mentioned above, external device 5 may be one of multiple device types, and may be interchangeable. For example external device 5 may be an illumination source such as light emitting diodes (LED), fluorescent tubes or laser sources, or any type of optical microscope such as linear optical microscopes (bright-field, epifluorescence, confocal, etc.) and non-linear optical microscopes (multi-photon excitation, second and third harmonic generation, coherent anti-Stockes Raman scattering, etc.) Illumination devices used with optical fibers 18 in the exemplary embodiment of FIG. 5 may be light emitting diodes (LED), fluorescent tubes or laser sources. For applications involving freely moving samples, the illumination source can be fiber coupled, or directly connected to the imaging cannula. For application requiring a high precision localization of the cannula 1, cannula 1 can be connected to high-precision positioning systems such as stereotaxic tools, or micromanipulators.

In each of the embodiments illustrated above, optical probe 2C may be provided by one of several exemplary structures: 1) A graded-index fiber providing a GRIN lens, generally with a diameter between 200 microns and 600 microns, numerical aperture in the range 0.25-0.6, a magnifying ratio of 1, an object working distance in the range 20-500 microns and field of view limited to the diameter of the lens to preserve spatial resolution; or 2) A rigid bundle of optical fibers, e.g., a hexagonal pack of multiple optical fibers with individual fibers diameter of 2-3 microns, a core percentage of the bundle higher than 70% and a numerical aperture in the range 0.5-1. Optical probe 2 may also serve as a magnifying lens, which may be a GRIN lens or rigid fiber bundle. When a GRIN lens is used, the length of the graded index fiber is adjusted to obtain a magnifying ratio of 1× to 10× between optical object plane 8 and optical image plane 9. When a rigid fiber bundle is used, the bundle of optical fiber is connected to an optical taper to form a relaying and magnifying rigid bundle of optical fibers. The magnifying ratio of the taper is in the range 1-10×.

While the invention has been particularly shown and described with reference to the preferred embodiment thereof, it will be understood by those skilled in the art that the foregoing and other changes in form, and details may be made therein without departing from the spirit and scope of the invention.

What is claimed:

1. A system for coupling an optical image of an object located within a biological sample to a location external to the biological sample, the system comprising:

an optical cannula providing a housing for securing an optical probe of the optical cannula within the sample, the housing having a stabilizer portion adapted for mounting the optical cannula to a surface of the sample and extending in a plane perpendicular to the optical probe to provide a contact area for bonding the optical cannula to the surface of the sample with an adhesive, wherein the housing further comprises a coupling for detachably receiving a connection, wherein the optical probe has a proximal end disposed at a position outside the sample and terminating within or proximate to an end of the coupling of the housing opposite the stabilizer portion, wherein the optical probe extends from the coupling through the stabilizer portion and into the sample and has a distal end for receiving light returning from the object, wherein the light returning from the object is coupled through the optical probe to the proximal end of the optical probe to provide the optical image of the object outside of the sample, and wherein the proximal end of the optical probe is mechanically integrated within the housing of the optical cannula so that the proximal end of the optical probe is mechanically aligned with the coupling and the stabilizer portion of the optical cannula and secured against movement with respect to the housing of the optical cannula; and a detachable connector for detachably connecting to the coupling of the optical cannula to supply the connection and providing a mechanical interface that is optically aligned with an optical axis of the optical probe by the attachment of the detachable connector to the coupling, whereby when the detachable connector is detached from the optical cannula, the optical cannula remains bonded to the surface of the sample and the distal end of the optical probe remains disposed within the sample.

2. The system of claim 1, wherein the detachable connector comprises a latch for securing the detachable connector to the coupling, the latch having a spring mechanism for securing the latch in a latched configuration wherein the latch is secured to the coupling.

3. The system of claim 2, wherein the latch comprises a flexible extension terminating in a hook, the flexible extension incorporated in the detachable connector extending along an outside surface of the detachable connector, wherein a profile of the flexible extension expands when compression force is applied to the detachable connector in a direction toward the sample, and wherein the coupling comprises a shoulder extending at least around a portion of a circumference of the coupler, wherein the hook is locked around the shoulder when the compression force is not applied to the detachable connector, wherein the spring mechanism applies a restoring force to the detachable connector in a direction away from the sample, and wherein the hook is released from the shoulder to permit removal of the detachable connector from the coupling when the compression force is applied to the detachable connector.

4. The system of claim 3, wherein the detachable connector further comprises:
   a compression nut attached to a threaded end of the detachable connector for providing the compression force by tightening the compression nut onto the detachable connector; and
   a spring for providing at least a portion of the restoring force by pushing the compression nut away from the detachable connector.

5. The system of claim 1, wherein the coupling has a recess for receiving a protrusion of the detachable connector, whereby the detachable connector is aligned with the optical cannula to align the optical axis of the optical probe with the detachable connector.

6. The system of claim 5, wherein a portion of the protrusion has a conical profile and wherein at least a portion of the recess has a conical bore, whereby the detachable connector self-aligns with the optical cannula.

7. The system of claim 1, wherein the detachable connector and the optical cannula comprise complementary keying features that prevent rotation of the optical cannula with respect to the detachable connector when securing the detachable connector to the optical cannula.

8. The system of claim 1, further comprising an optical device for receiving the optical image of the object, wherein the detachable connector is integral to a housing of the optical device.

9. The system of claim 1, wherein the optical probe comprises a cylindrical gradient-index lens or fiber bundle secured to and extending through an extension portion of the optical cannula, wherein the distal end of the optical probe is a polished surface of the gradient-index lens or fiber bundle for receiving the light returning from the object.

10. The system of claim 1, wherein the optical cannula further comprises a tube for conducting a fluid and disposed along a length of optical probe, wherein the tube has a distal end terminating adjacent to the distal end of the optical probe.

11. The system of claim 1, wherein the optical cannula further comprises an electrode for conducting an electric potential and disposed along a length of optical probe, wherein the electrode has a distal end terminating adjacent to the distal end of the optical probe.

12. A method of coupling an optical image of an object located within a biological sample to an optical device, the method comprising:
   mounting an optical cannula that provides a housing for securing an optical probe of the optical cannula within the biological sample by attaching a stabilizer portion of the optical cannula that extends in a plane perpendicular to the optical probe to a surface to the biological sample by bonding a contact area of the stabilizer portion of the optical cannula to the surface of the biological sample with an adhesive, while inserting the optical probe of the optical cannula into the biological sample, whereby a distal end of the optical probe receives the light returning from the object, wherein the light returning from the object is coupled through the optical probe to a proximal end of the optical probe to provide the optical image of the object outside of the sample, and wherein the optical probe is mechanically integrated within the housing of the cannula so that the proximal end of the optical probe is mechanically aligned with the coupling and the stabilizer portion of the optical cannula and secured against movement with respect to the housing of the optical cannula;
   optically coupling the optical device to the proximal end of the optical probe by mechanically coupling a detachable connector coupled to the optical device to the coupling of the optical cannula, wherein the optical device is aligned with an optical axis of the optical probe by the attachment to the connector to the coupling; and
   detaching the detachable connector from the optical cannula so that the optical cannula remains bonded to the surface of the sample and the distal end of the optical probe remains disposed within the sample.

13. The method of claim 12, further comprising securing the detachable connector to the coupling by a latch forming part of the detachable connector, the latch having a spring mechanism for securing the latch in a latched configuration wherein the latch is secured to the coupling.

14. The method of claim 13, wherein the latch comprises a flexible extension terminating in a hook, the flexible extension incorporated in the detachable connector extending along an outside surface of the detachable connector, wherein a profile of the flexible extension expands when compression force is applied to the detachable connector in a direction toward the sample, and wherein the coupling comprises a shoulder extending at least around a portion of a circumference of the coupler, wherein the hook is locked around the shoulder when the compression force is not applied to the detachable connector, wherein the spring mechanism applies a restoring force to the detachable connector in a direction away from the sample, and wherein the hook is released from the shoulder to permit removal of the detachable connector from the coupling when the compression force is applied to the detachable connector.

15. The method of claim 14, wherein the detachable connector further comprises:
   a compression nut attached to a threaded end of the detachable connector for providing the compression force by tightening the compression nut onto the detachable connector; and
   a spring for providing at least a portion of the restoring force by pushing the compression nut away from the detachable connector.

16. The method of claim 12, wherein the mechanically coupling inserts a protrusion of the detachable connector into a recess of the coupler of the optical cannula to align the optical axis of the optical probe with the optical device.

17. The method of claim 16, wherein a portion of the protrusion has a conical profile and wherein at least a portion of the recess has a conical bore, whereby the detachable connector self-aligns with the optical cannula during the mechanically coupling.

18. The method of claim 12, preventing rotation of the optical cannula with respect to the detachable connector when securing the detachable connector to the optical cannula by aligning complementary keying features of the detachable connector and the optical cannula.

19. The method of claim 12, further comprising introducing a fluid to the sample via a tube disposed along a length of optical probe, wherein the tube has a distal end terminating adjacent to the distal end of the optical probe.

20. A system for coupling an optical image of an object located within a biological sample to a location external to the biological sample, the system comprising:

an optical cannula providing a housing for securing an optical probe of the optical cannula within the sample, the housing having a stabilizer portion adapted for mounting the optical cannula to a surface of the sample and extending in a plane perpendicular to the optical probe to provide a contact area for bonding the optical cannula to the surface of the sample, wherein the housing further comprises a coupling for detachably receiving a connection, wherein the optical probe has a proximal end disposed at a position outside the sample and terminating within or proximate to an end of the coupling of the housing opposite the stabilizer portion, wherein the optical probe extends from the coupling through the stabilizer portion and into the sample and has a distal end for receiving light returning from the object, wherein the light returning from the object is coupled through the optical probe to the proximal end of the optical probe to provide the optical image of the object outside of the sample, and wherein the proximal end of the optical probe is mechanically integrated within the housing of the optical cannula so that the proximal end of the optical probe is mechanically aligned with the coupling and the stabilizer portion of the optical cannula and secured against movement with respect to the housing of the optical cannula; and a detachable connector for detachably connecting to the coupling of the optical cannula to supply the connection and providing a mechanical interface that is optically aligned with an optical axis of the optical probe by the attachment of the detachable connector to the coupling, wherein the detachable connector comprises a latch for securing the detachable connector to the coupling, the latch formed from spring material forming an extension terminating in a hook extending along an outside surface of the detachable connector, wherein a profile of the flexible extension expands when compression force is applied to the detachable connector in a direction toward the sample, and wherein the coupling comprises a shoulder extending at least around a portion of a circumference of the coupler, wherein the hook is locked around the shoulder when the compression force is not applied to the detachable connector, wherein the spring mechanism applies a restoring force to the detachable connector in a direction away from the sample, and wherein the hook is released from the shoulder to permit removal of the detachable connector from the coupling when the compression force is applied to the detachable connector, whereby when the detachable connector is detached from the optical cannula, the optical cannula remains bonded to the surface of the sample and the distal end of the optical probe remains disposed within the sample.

21. The method of claim 20, further comprising applying an electric potential to or receiving an electrical potential from the sample via an electrode disposed along a length of optical probe, wherein the electrode has a distal end terminating adjacent to the distal end of the optical probe.

* * * * *

UNITED STATES PATENT AND TRADEMARK OFFICE
CERTIFICATE OF CORRECTION

PATENT NO. : 10,016,136 B2
APPLICATION NO. : 14/310012
DATED : July 10, 2018
INVENTOR(S) : Labrie et al.

Page 1 of 1

It is certified that error appears in the above-identified patent and that said Letters Patent is hereby corrected as shown below:

Column 10, Line 28, the claim reference numeral '20' should read --Claim 12--.

Signed and Sealed this
Fourth Day of December, 2018

Andrei Iancu
*Director of the United States Patent and Trademark Office*